(12) United States Patent
Franklin

(10) Patent No.: US 7,813,807 B2
(45) Date of Patent: Oct. 12, 2010

(54) SYSTEMS AND METHODS FOR TREATMENT OF RETINOPATHY AND OTHER EYE DISEASES

(75) Inventor: Amie B Franklin, Mill Valley, CA (US)

(73) Assignee: Oxyband Technologies, Inc., San Francisco, CA (US)

( * ) Notice: Subject to any disclaimer, the term of this patent is extended or adjusted under 35 U.S.C. 154(b) by 659 days.

(21) Appl. No.: 11/464,680

(22) Filed: Aug. 15, 2006

(65) Prior Publication Data

US 2008/0046028 A1    Feb. 21, 2008

(51) Int. Cl.
*A61N 1/00* (2006.01)
(52) U.S. Cl. .............................. 607/53; 607/3
(58) Field of Classification Search .............. 607/53, 607/54, 3
See application file for complete search history.

(56) References Cited

U.S. PATENT DOCUMENTS

| | | | | |
|---|---|---|---|---|
| 4,628,933 A | * | 12/1986 | Michelson | 607/53 |
| 5,193,540 A | * | 3/1993 | Schulman et al. | 607/61 |
| 5,314,458 A | * | 5/1994 | Najafi et al. | 607/116 |
| 6,185,452 B1 | * | 2/2001 | Schulman et al. | 604/20 |
| 6,389,317 B1 | * | 5/2002 | Chow et al. | 607/54 |
| 2004/0172100 A1 | * | 9/2004 | Humayun et al. | 607/54 |

* cited by examiner

*Primary Examiner*—George R Evanisko
(74) *Attorney, Agent, or Firm*—Donald R. Boys; Central Coast Patent Agency, Inc.

(57) ABSTRACT

An oxygen-producing device for aiding in treatment of diseases and conditions of the human eye has a power supply with an electrical output, and at least one pair of electrodes, one electrode of the pair coupled to the electrically positive output and the other coupled to the electrically negative output. The device is characterized in that the device is sized to occupy no more than one fortieth of the volume of an average human eye, and the power supply is enabled to provide a DC voltage of at least 1.2 volts over a period of time.

5 Claims, 4 Drawing Sheets

SYSTEMS AND METHODS FOR TREATMENT OF RETINOPATHY AND OTHER EYE DISEASES

BACKGROUND OF THE INVENTION

1. Field of the Invention

The present invention is in the area of therapeutic devices and methods for treating diseases and conditions of the human eye, and related more particularly to systems for supplying oxygen for treatment.

2. Discussion of the State of the Art

Importance of oxygen for the human eye is well understood, and Retinal hypoxia—a reduction in the delivery of oxygen to the retina—has been implicated as an underlying cause of a number of eye (retinovascular) diseases such as diabetic retinopathy, diabetic macular edema, age-related macular degeneration, sickle cell disease, retinopathy of prematurity, familial exudative retinopathy, retinal vascular occlusions, ocular ischemic syndrome, and other related conditions. As such diseases progress, there develops some combination of relative impermeability of normally permeable tissues to oxygen diffusion or a closure of retinal capillaries, leading to hypoxia. The hypoxia, in turn, stimulates the production of vascular endothelial growth factor (VEGF) leading to subretinal, intraretinal, or extraretinal neovascularization. VEGF also stimulates vascular permeability and leakage of both normal and new vessels leading to retinal edema and hemorrhage. Oxygen has been shown to be beneficial to treat these types of retinopathy.

Even though the value of oxygen to the human eye has been well-known, as discussed above, oxygen as an intraocular therapeutic agent to prevent and treat eye disease has not been routinely used because it has not been possible to sustainably deliver oxygen to the target tissues in adequate quantities into the eye to meet metabolic requirements for effective management and treatment of these and other ocular diseases.

The supply of oxygen to the retina is believed by the inventor to be pertinent to diseases such as macular degeneration and diabetic retinopathy. Under normal healthy conditions oxygen is delivered to the retina via a dual blood supply, a system called the choroid supplying the outer part of the retina, which is not heavily regulated, and a separate inner retinal vascular system that is highly influenced by metabolic feedback from the tissue within the retina, so as to maintain relatively constant oxygen supply.

Oxygen may play an important role in therapeutic treatment of eye diseases. In a recent study at Johns Hopkins (9 eyes were measured), patients with chronic Diabetic Macular Edema (DME) received 4 L/min of inspired oxygen by nasal cannula for 3 months. After 3 months of oxygen therapy, nine of nine eyes with DME at baseline showed a reduction in thickness of the center of the macula. Foveal thickness (FTH) above the normal range was reduced by an average of 43.5% (range, 14%-100%), excess foveolar thickness (CEN) was reduced by an average of 42.1% (range, 13%-100%), and excess macular volume was reduced by an average of 54% (range, 35%-100%), P=0.0077. Three eyes showed improvement in Visual Acuity by at least 2 lines, one by slightly less than 2 lines, and five eyes showed no change. Three months after discontinuation of oxygen, five of the nine eyes showed increased thickening of the macula compared with when oxygen was discontinued. Researchers concluded supplemental oxygen may decrease macular thickness due to DME, suggesting that retinal hypoxia is involved in the development and maintenance of DME. The present invention is intended to treat eye diseases.

An example of such a disease is diabetic retinopathy (damage to the retina) which is caused by complications of diabetes mellitus and can eventually lead to blindness. Diabetic retinopathy affects up to 80% of all diabetics who have had diabetes for 15 years or more Despite these intimidating statistics, research indicates that at least 90% of these new cases could be reduced with proper and vigilant treatment.

In diabetic retinopathy, as blood vessels become blocked and oxygen deprivation begins, excess growth factors start to be released to promote the growth of new blood vessels, in a process called 'neovascularization' in the art. Among these various growth factors, the one termed VEGF, introduced above, is found in the endothelial cells lining these blood vessels. Retinal blood vessels have three times as many receptors for VEGF as vessels elsewhere, and oxygen deficit dramatically raises VEGF levels. VEGF is believed to play a major role in stimulating neovascularization, and also in vascular leakage in the eye. Other treatments such as laser treatments that are used to treat proliferative diabetic retinopathy work in part by lowering levels of growth factors like VEGF. Antibodies and other inhibitors of VEGF are also beginning to appear in research designed to stop the growth of cancers, and some of these are being used to treat neovascular proliferation, both choroidal and inner retinal. Therapies used to treat macular degeneration and diabetic macular edema attempt to prevent VEGF over-expression or block its pathological effects in the retina. Blockage of capillaries is found in background retinopathy, but a more serious form of blockage to blood vessels occurs in preproliferative and proliferative retinopathy. Capillary drop-out impairs the delivery of oxygen and other nutrients that are required to maintain cell health. Oxygen deficit in turn triggers cell damage and release of growth factors. Although there are therapeutics to reduce or inhibit the effect of VEGF, there are no known therapeutic inventions to improve the supply of oxygen to the retina and therefore stop the trigger release of growth factors which play a major role in causation of choroidal and inner retinal neovascularization.

Retinal oxygen demand under normal conditions is very high (even higher than for the brain) and may be affected by different conditions. The relative contribution of the blood vessels of the inner retinal vasculature and those of the choroid—a layer of vascular tissue external to the retina—to the oxygenation of the retina, in health and disease, is not sufficiently understood. Human retinal oxygen consumption has been difficult to measure because any anesthesia used for in vivo measurements reduces the blood flow to the eye and the invasive nature of the measurement procedure prohibits the amount of human data that can be collected.

It is understood from oxygen microelectrode studies in animals with circulatory patterns similar to those of humans, that the inner and outer halves of the retina are different domains in terms of oxygen. Failure of inner retinal circulation (ischemia) leads to tissue hypoxia that underlies vasoproliferation in diabetic retinopathy, retinopathy of pre maturity, and the other inner retinovascular diseases.

In the macula, photoreceptors sit on a layer of pigment cells, called the retinal pigment epithelium, (RPE). These very active photoreceptors must be continuously supplied by new light-sensitive material. Used light-sensitive material is continuously absorbed by the pigment epithelium and recycled to be re-used again. This process requires oxygen and other nutrients supplied by the fine blood vessels of the choroid (choriocapillaris). Thickening of the outer RPE basement membrane, the primary pathophysiologic finding in macular degeneration, leads to diminished ability to deliver oxygen to the macular region of the retina. When the renewal process of the photoreceptors fails, the photoreceptors die and so also does the pigment epithelium. This causes a dry form of macular degeneration. Distressed photoreceptors and pigment epithelium release VEGF because they need more oxygen. As a response, the choriocapillaris attempts to make new vessels that intend to supply more oxygen to the photoreceptors (choroidal neovascularization). However, the new vessels are disorderly and have defective walls that tend to leak and bleed, damaging the macula further. This is called the wet form of macular degeneration. This, in turn, leads to exudative macular detachment and damaged photoreceptors, the main findings of age-related macular degeneration.

Choroidal blood flow is not regulated metabolically, so systemic hypoxia and elevated intraocular pressure both lead to decreases in choroidal $PO_2$ (the partial pressure of oxygen) and photoreceptor oxygen consumption. The same lack of regulation allows choroidal $PO_2$ to increase dramatically during hyperoxia, offering a potential for systemic oxygen to be used therapeutically in retinal vascular occlusive diseases and retinal detachment. However, to the knowledge of the inventor, there are no effective means presently available for delivering oxygen inside the eye to the retina. What is clearly needed therefore, are reliable and sustainable apparatus and methods for delivering oxygen inside the eye, particularly to the retina, for treatment of eye conditions and diseases.

SUMMARY OF THE INVENTION

In an embodiment of the invention an oxygen-producing device is provided comprising a power supply with an electrically positive and an electrically negative output, and at least one pair of electrodes, one electrode of the pair coupled to the electrically positive output and the other coupled to the electrically negative output. The device is characterized in that the device is sized to occupy no more than one fortieth of the volume of an average human eye, and the power supply is enabled to provide a DC voltage of at least 1.2 volts.

In one embodiment the power supply comprises a nano-battery rechargeable by magnetic induction. In another embodiment the power supply comprises a pair of cantilevered strips coupled to the electrodes, one of which strips is composed at least in part of a radioactive material that emits electrons, and the other is a metal strip, such that electrons emitted from the first strip collect on the second strip producing an electrical potential that appears across the electrodes. Also in one embodiment at least one of the strips is of a flexibility that the opposite charges cause the flexible strip to deflect toward the other strip, resulting over time in a proximity of the strips that results in discharge of the potential, after which the flexible strip returns to the un-deflected state, and the charge begins to rebuild.

In one embodiment there may be an envelope enclosing the electrodes, the envelope including a port for discharge of gases from within the envelope. Also in an embodiment there may be a charge of sterile liquid initially within the envelope to serve as material for production of oxygen. The liquid may be water or hydrogen peroxide.

In another aspect of the invention a method for providing oxygen in a human eye for treatment and therapeutic purposes is provided, comprising the steps of (a) coupling a pair of electrodes to a power supply in a manner to produce at least 1.2 volts across the electrodes for a period of time, with the power supply and electrode device thus produced defining a volume of no more than one fortieth of the average volume of a human eye; and (b) positioning the device in the vitreous of a human eye.

In some embodiments step (b) comprises steps of placing the nano- or micro-devices in solution and injecting them through a needle inserted in the eye to a desired position, urging the device from the needle into the eye, and withdrawing the needle.

In some embodiments the power supply may be a nano-battery rechargeable by magnetic induction. In another embodiment the power supply may comprise a pair of cantilevered strips coupled to the electrodes, one of which strips is composed at least in part of a radioactive material that emits electrons, and the other is a metal strip, such that electrons emitted from the first strip collect on the second strip producing an electrical potential that appears across the electrodes. In some cases one of the strips is of a flexibility that the opposite charges cause the flexible strip to deflect toward the other strip, resulting over time in a proximity of the strips that results in discharge of the potential, after which the flexible strip returns to the un-deflected state, and the charge begins to rebuild.

In some embodiments there may be an envelope enclosing the electrodes, the envelope including a port for discharge of gases from within the envelope, and in some of these embodiments there may an initial charge of sterile liquid within the envelope to serve as material for production of oxygen. The material in some cases may be water or hydrogen peroxide.

BRIEF DESCRIPTION OF THE DRAWING FIGURES

DETAILED DESCRIPTION OF THE INVENTION

Figure 1:
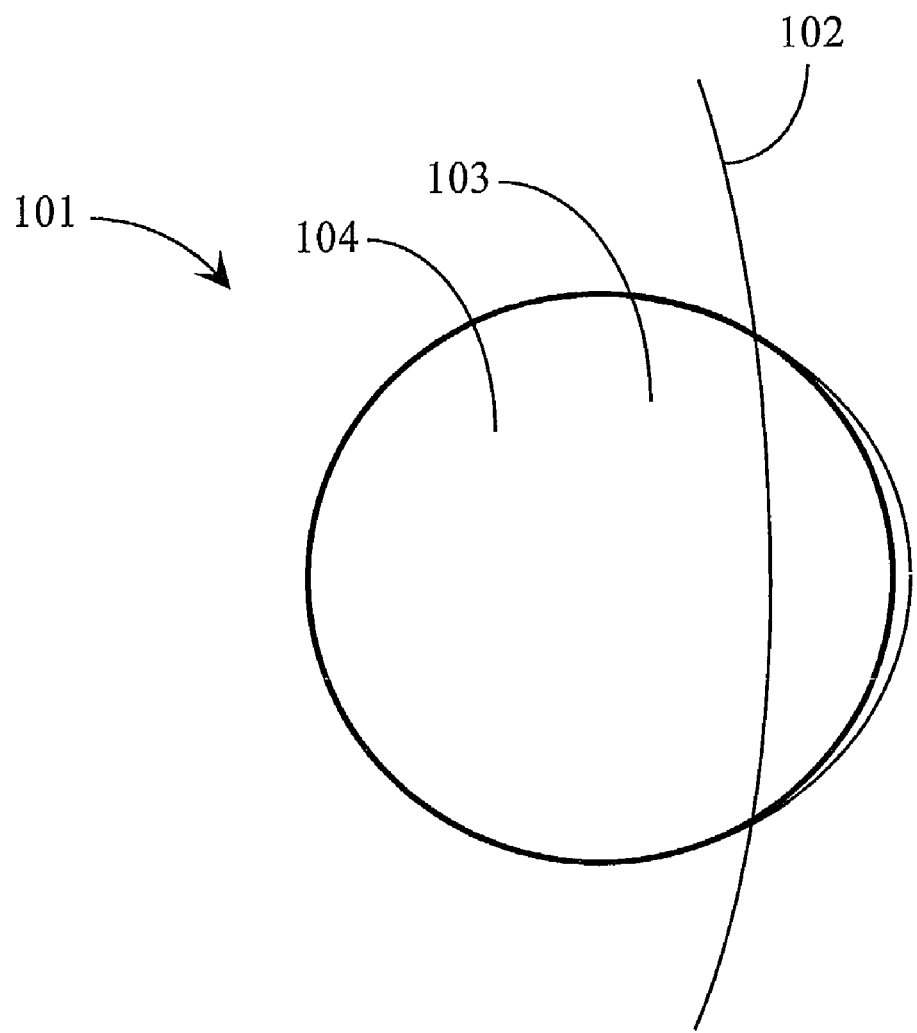
FIG. 1 is an illustration of a human eye, and comparative size of an apparatus of the invention for providing oxygen in the eye.

An object of the present invention is to produce an environment in the human eye that is enhanced in free oxygen, that is oxygen-rich, or at least more so then the typical (morbid or pathological) vitreous content of the eye. FIG. 1 is a simplistic illustration of a human eye 101 having a very small device 104 implanted in the vitreous, and is provided to provide comparative sizes for better understanding of examples of the present invention. The vitreous of the eye is typically somewhat viscous, and has an aqueous component. The vitreous typically becomes more fluid with advancing age.

The human eye 101 in FIG. 1 is typically less than one inch from front to back, perhaps an average of about 23 millimeters. For a device implanted in the eye to not be a problem for vision or irritation, the device 104 must be quite small, and the position of placement will also be important. Sizes and dimensions can vary, but the devices illustrated and described herein will typically be of a size that would occupy an envelope no more than two or three millimeters on a side, and in most cases smaller yet.

Figure 2:
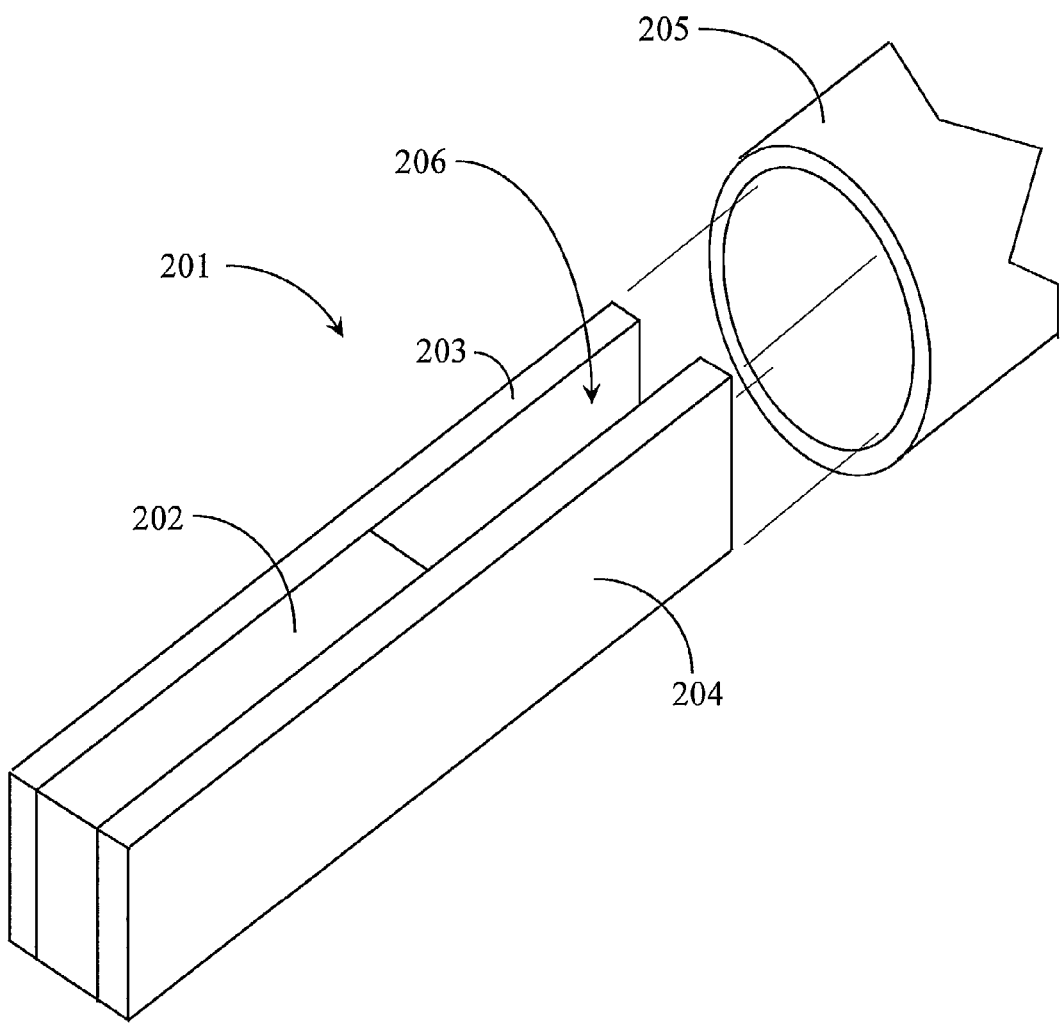
FIG. 2 is an illustration of an apparatus for supplying oxygen in a human eye in an embodiment of the present invention.

FIG. 2 is an illustration of an apparatus 201 in one embodiment the present invention that produces oxygen by electrolysis (traditionally used to produce hydrogen) and can be implanted in the vitreous of a human eye. Device 201 comprises a power supply 202, and a pair of electrodes 203 and 204, in which the electrodes contact the body of the power supply along opposite sides of the body, and extend for a distance beyond the body, providing a space 206 between the electrodes. Tubing 205 represents the action end of a surgical needle, and the cross-section of the power supply and electrodes is of a size that the assembly in one direction may pass through the eye of the needle or canulae or in a solution through either.

The illustration of an end of a surgical needle in FIG. 2 is not to suggest that a device 201 may be aspirated into a syringe, and then injected along with a fluid into a user's eye, although this means of placement might in some cases be useful. A preferable system for placement would use a portion of a surgical needle, but a device 201 would be placed in the hollow shaft of the needle portion, close to the end, under a microscope or other magnification apparatus. The needle portion comprises a rod in the hollow shaft that may be manipulated. After placement of the device 201, the needle portion is dipped in perhaps a saline solution, or another antiseptic, anti-bacterial fluid, the needle is inserted into the eye of the person to be treated, with the point of the needle placed at the point in the eye where the device is desired to be placed, then the device 201 is pushed out of the needle by translating the rod forward, pushing the device 201 out of the needle and into the eye. The needle is then withdrawn. (If the size is 2-3 mm then it would be more properly called a cannula than a needle.)

Electrodes 203 and 204 in this embodiment are metal film, and power supply body 202 is of a non-electrically-conductive material, which may be ceramic, such that electrodes 203 and 204 are never electrically shorted. Output contacts on each side of power supply 202 make contact with electrodes 203 and 204 in such a manner that a voltage may be induced across electrodes 203 and 204. The aqueous of the human eye, when apparatus 201 is implanted in the vitreous, will fill space 206, and voltage induced across the electrode gap will disassociate water in the aqueous into oxygen and hydrogen.

Both the oxygen and the hydrogen produced will by taken into solution in the aqueous of the eye. At least a portion of the oxygen will be available as therapeutic material for regeneration and treatment of various diseases and conditions of the human eye.

In this embodiment of apparatus 201, water from the aqueous environment in the vitreous is electrolyzed to form oxygen by applying a voltage of 1.2 volt DC minimum potential across electrodes 203 and 204 of the device by power supply 202. The reaction produced in electrolysis is $2H_2O \rightarrow 2H_2 + O_2$. The hydrogen byproduct from electrolysis is eliminated by absorption into the bloodstream of the individual.

In some treatment procedures more than one oxygen generator of the sort described may be injected into a human eye to maximize production of oxygen, and multiple devices may be placed at different position in the eye to provide oxygen generation over a planned region of the eye.

Power supply 202 in some embodiments may comprise an onboard battery system, which in some embodiments might be a rechargeable system responsive to an ambient alternating magnetic field inductively producing an electric current in a charging circuit coupled to power supply 202.

In an alternative embodiment a bio-based micro-battery might be used as well. Additionally, the apparatus might also be powered by a miniaturized nickel-based nuclear cell, which could provide power consistently for an indefinite period. The bio-battery in one embodiment might be based on synthetic ion transport proteins. Ionic species of a gas may be produced at one electrode, where the produced ionic species is transported across an ion-permeable membrane, and the transported ionic species react at a second electrode to be converted into a molecule which produces a net change of concentration of oxygen.

Figure 3:
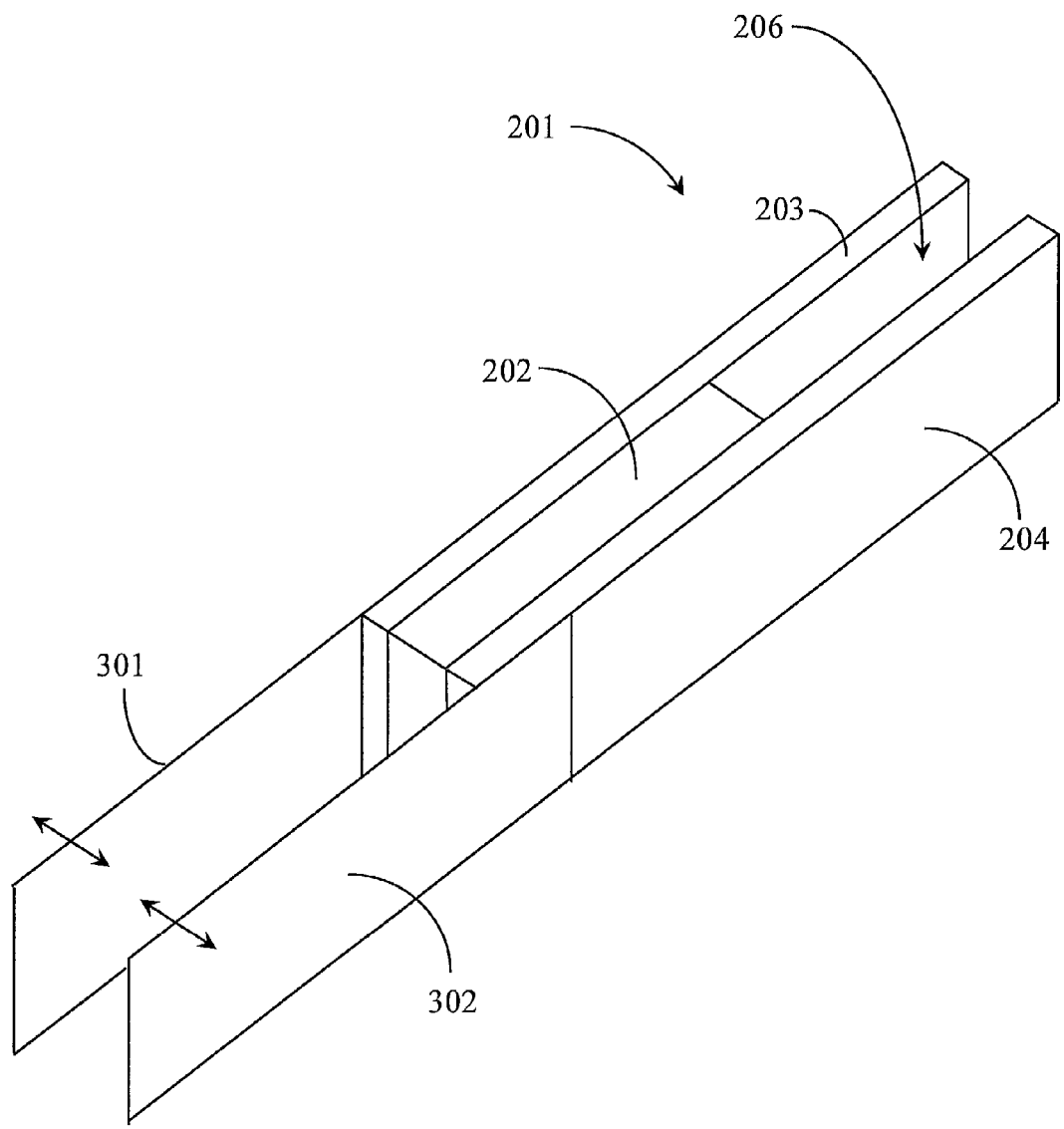
FIG. 3 is an illustration of an apparatus as in FIG. 1, including a novel power supply in an embodiment of the invention.

FIG. 3 illustrates schematically a nickel-based nuclear cell, as briefly described above, integrated to a pair of electrodes as described with reference to FIG. 2. In this case element 202 is a simply a spacer for insulating the two electrodes from one another electrically so an electrical potential may be established across the electrodes. A metal strip 301, which may be about one millimeter wide and two millimeters long (the average human eye is 23 mm long) and 60 micrometers (millionths of a meter) thick is spaced apart from a thin film of radioactive nickel-63, which emits beta particles (electrons). The emitted electrons collect on the metal strip, which may be, for example, copper, producing a negative charge (buildup of excess electrons with no path for an electrical current). The isotope film, losing electrons, becomes positively charged relative to the opposed metal strip.

The metal strip 301, that becomes negatively charged, is congruent with electrode 203, and the electron-emitting strip 302 is congruent with electrode 204. Therefore the voltage induced between metal strip 301 and strip 302 appears also across electrodes 203 and 204. As the voltage builds up, strips 301 and 302, cantilevered as shown, deflect toward one another until at a close approach a current flows and the charge is dissipated. As soon as the charge dissipates, the voltage begins to build again.

The spacing and geometry is controlled to produce a voltage that exceeds 1.2 volts D.C. considered a minimum to drive electrolysis of water to produce oxygen under these conditions. The voltage may be allowed to build to somewhat above 1.2 volts in operation. The net result is an oscillating voltage across electrodes 203 and 204, which produces electrolysis for the time that the voltage exceeds 1.2 volts D.C.

In some cases the thickness of the strips is controlled such that only one (say the metal strip 301) will deflect significantly under the voltage influence. Also, in some cases there need not be separate electrodes, as the metal strip and the radioactive nickel strip serve also as the electrodes for electrolysis.

In yet another embodiment the battery might be a tiny solar panel, which might in some embodiments be implemented as a contact lens, or power might be provided by a solar-powered chip.

Also in an alternative embodiment oxygen might be supplied in the human eye by a solar powered nano-motor that could produce oxygen. Here is one possibility for the solar nano motor. In such a motor absorption of sunlight by one of two stoppers, a light-harvesting one, causes transfer of one electron to a station A, which is deactivated as far as wanting a ring to encircle it. As a consequence, the ring moves to its second port of call, station B. Station A is subsequently reactivated by the return of the transferred electron to the light-harvesting stopper, and the ring moves back to this station.

In some cases an oxygen generator as described above may generate oxygen substantially without generating free hydrogen using a multilayer electrolyzer sheet having a proton exchange membrane sandwiched by an anode layer and a cathode layer. Inductive energy transfer could be targeted for periods of dark adaptation, or sleep cycles, as there is evidence that retinal hypoxia is greatest during periods of dark adaptation and high rod metabolic activity.

Radioactive isotopes can continue to release energy over periods ranging from weeks to decades. The half-life of nickel-63, for example, is over 100 years. So a device thus powered might provide oxygen to a user's eye for a long period of time.

A moving cantilever may also directly actuate a linear device or can move a cam or ratcheted wheel to produce rotary motion. A magnetized material attached to the rod can generate electricity as it moves through a coil. Or a nano battery which incorporates covering the electrodes with millions of tiny filaments called nanotubes. Each nanotube is 30,000 times thinner than a human hair. Nanotube filaments increase the surface area of the electrodes and provide enhanced capacitance to store more energy. The nano battery, which has the longevity of present battery technology, has the speed of a capacitor. Or a battery may consist of a miniaturized galvanic cell comprising a cathode, anode, and electrolyte.

In another aspect of the invention water may be supplied with the device 201 and may be stored with the device and consumed from its own reservoir. This reservoir could be refillable or single use. Advantages of supplying water would be that you wouldn't disturb the balance/ratio of other ingredients suspended in the fluid of the eye, and prevent contamination of the electrodes.

Figure 4:
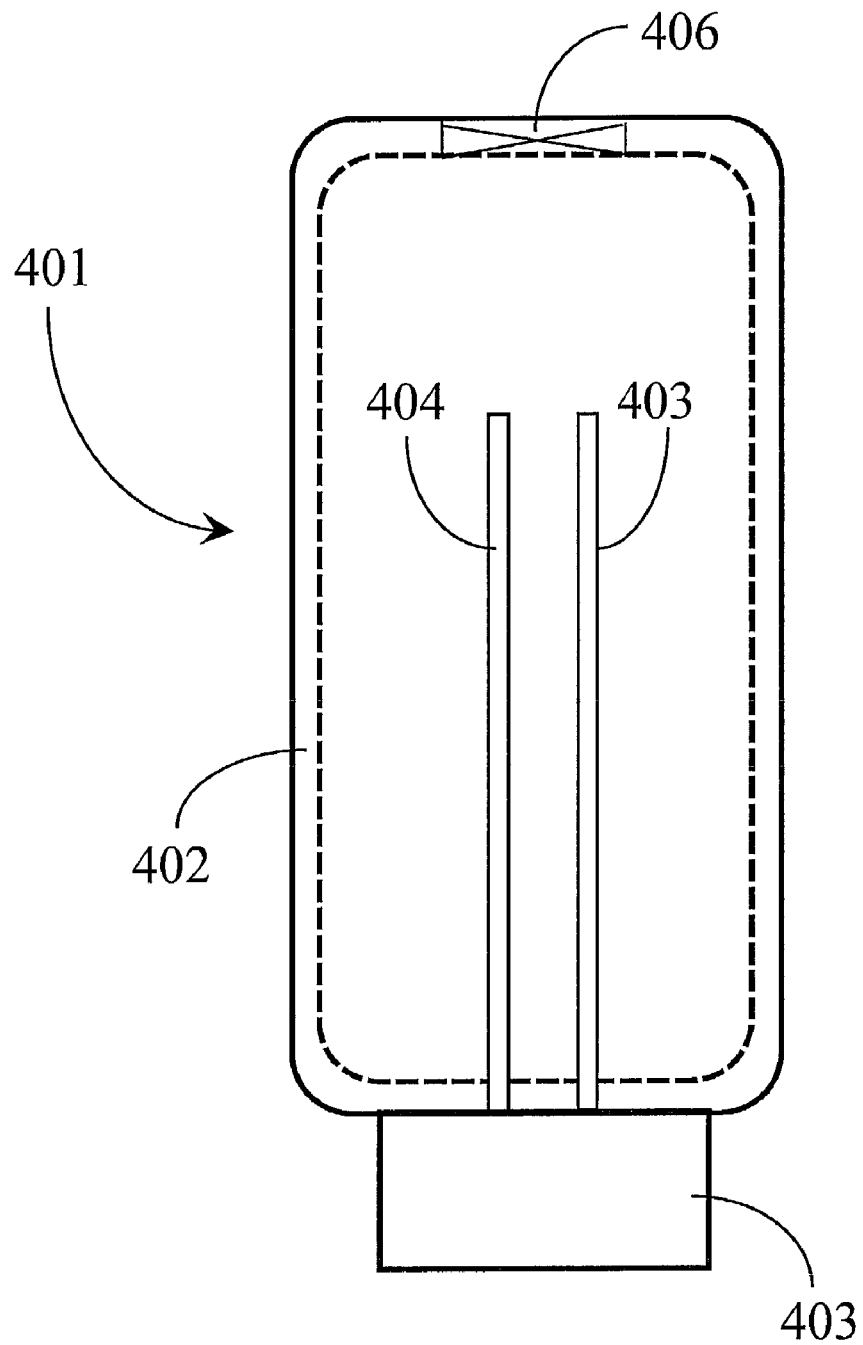
FIG. 4 illustrates an alternative embodiment of the present invention.

FIG. 4 illustrates schematically a water-filled capsule 401 having electrodes 404 and 403 spaced apart in fluid inside the capsule. Capsule 401 comprises a glass envelope 402 in this embodiment, although the envelope might be of other benign material in other embodiments. Electrodes 403 and 404 seal through glass envelope 402, and connect to power supply 403, which may be a power supply of any nature described for the purpose in this specification, such as a miniature battery, a nuclear cell, and so forth. At least one region of envelope 402 comprises a permeable membrane 406, which is a hydrophobic but gas-permeable membrane that lets gas out but keeps the liquid in. Also in some embodiments the exit of gas from the envelope might be through a one-way valve that might be accomplished by a pierced flexible polymer material, a needle hole in a rubber plug by analogy.

In one embodiment the liquid with which the capsule is filled is water, and oxygen is produced by electrolysis, as described above, and escapes, along with the hydrogen produced, through the membrane or one-way valve. It should be noted that the gases produced by electrolysis create a pressure in the capsule, but gases are very quickly absorbed in solution by the water. The capsule can be expected under a steady-state operation to expel some fluid, due to the increased pressure, the fluid being oxygen rich. When the operation ceases, due to either being switched off or the power supply failing, the pressure should return to equilibrium with the surrounding environment. Oxygen produced will be expected to interact in the eye in beneficial ways in treatment of conditions of the eye as described herein, but likely not all of the oxygen produced will be so employed. Much may simply be removed through the natural action of the fluids with the blood supply. Hydrogen produced will also be removed over time by the same mechanism in many embodiments.

In some embodiments one might use mems technology to release the water from a pre-filled reservoir to the electrolyzing electrodes at just a desired rate, or it could be rate controlled by using the water supply controller as a preset or remotely controlled selectable level.

In some embodiments another oxygen-rich liquid might be used instead of or in conjunction with water in such a capsule. Hydrogen peroxide is a possibility. The boding energies for some oxygen-rich liquids are less than that for water, and might be expected to electrolyze to produce free oxygen more readily than water.

In yet another aspect of the invention water enriched with oxygen-filled nanobubbles could be used either alone or in conjunction with another device to provide oxygen in the human eye. Such water could augment or complement any device providing oxygen such as the devices described herein. In some case enriched water may be provided along with implanting a device according to the invention.

In another aspect of the invention the oxygen-producing utilizes a photosynthetic process. Natural photosynthesis is a process by which light from the sun is converted to chemical energy. The chemical energy he referred to comes from the breakdown of carbon dioxide ($CO_2$) and water ($H_2O$), driven by photons of light, and leads to production of carbohydrates that nourish plants and of oxygen ($O_2$), which is vital to aerobic organisms.

The conversion of unusable sunlight energy into usable chemical energy, is associated with the actions of the green pigment chlorophyll in nature. The photosynthetic process uses water and releases oxygen. The overall reaction of this process is: $6H_2O+6CO_2 \rightarrow C_6H_{12}O_6+6O_2$ or six molecules of water plus six molecules of carbon dioxide produce one molecule of sugar plus six molecules of oxygen. To run this reaction a plant utilizes a catalyst—chlorophyll—and the energy from the sun to aid in the decomposition of water. While the chlorophyllic reaction does produce diatomic oxygen gas, it does not produce the hydrogen in a gaseous form. The hydrogen released from the water is used for the formation of glucose.

In this aspect of the invention the device can be implanted in areas of the eye such as the vitreous to produce the oxygen needed by the retina. The device utilizes a process similar to photosynthesis to produce energy+oxygen.

In this aspect the photosynthetic process, uses the light coming through the ocular media to and from the retina, traps it in the vitreous and utilized by the device to power a process similar to photosynthesis. The device can involve photo-induced electron transport across membranes and is carried out by pigment molecules organized into reaction centers by membrane-spanning proteins. The resulting transmembrane electrochemical potential is then coupled to the movement of protons across the membrane. Photo-induced electron transport followed by thermal electron transfer, leading to charge separation over distances of 8 nm. As shown in FIG. 5, this has been demonstrated in artificial mimics of the photosynthetic reaction centre comprising covalently linked electron donors and acceptors. The photosynthetic apparatus transports protons across a lipid bilayer when illuminated. At the centre is a molecular 'triad', consisting of an electron donor and acceptor linked to a photosensitive porphyrin group. This triad is incorporated into the bilayer of a liposome. When excited, it establishes a reduction potential near the outer surface of the bilayer and an oxidation potential near its inner surface. In response to this redox potential gradient, a freely diffusing quinone molecule alternates between its oxidized and reduced forms to ferry protons across the bilayer with an overall quantum yield of 0.004, creating a pH gradient between the inside and outside of the liposome (Gali Steinberg-Yfrach, Paul A. Liddell, Su-Chun Hung, Ana L. Moore, Devin Gust and Thomas A. Moore).

The invention could also take among other forms of a hexad, or six-part, nano-particle made of four zinc tetraarylporphyrin molecules, $(P_{ZP})_3$—$P_{ZC}$, a free-base porphyrin, and a fullerene molecule, P—$C_{60}$ (Devens and Gust). When one of the three outer zinc porphyrin rings is excited by light energy, the energy is transferred through the central zinc porphyrin to the free-base porphyrin, which is connected to the fullerene. The energy causes the free-base porphyrin and fullerene to exist in an excited state where there is electron transfer and charge separation. The free-base porphyrin and fullerene then decay, resulting in recombination and an output of electrochemical energy plus the byproduct of Oxygen to be used to treat diseases in the eye.

In natural photosynthesis the thylakoid is responsible for PhotoSystem II (PS II), PhotoSystem I (PS I), or with antenna proteins feeding energy into these photosystems. PS II is the complex where water splitting and oxygen evolution occurs. Upon oxidation of the reaction center chlorophyll in PS II, an electron is pulled from a nearby amino acid (tyrosine) which is part of the surrounding protein, which in turn gets an electron from the water-splitting complex. From the PS II reaction center, electrons flow to free electron carrying molecules (plastoquinone) in the thylakoid membrane, and from there to another membrane-protein complex, the cytochrome $b_6f$ complex. The other photosystem, PS I, also catalyzes light-induced charge separation in a fashion basically similar to PS II: light is harvested by an antenna, and light energy is transferred to a reaction center chlorophyll, where light-induced charge separation is initiated. However, in PS I electrons are transferred eventually to NADP (nicotinamid adenosine dinucleotide phosphate), the reduced form of which can be used for carbon fixation. The oxidized reaction center chlorophyll eventually receives another electron from the cytochrome $b_6f$ complex. Therefore, electron transfer through PS II and PS I results in water oxidation (producing oxygen) and NADP reduction, with the energy for this process provided by light (2 quanta for each electron transported through the whole chain).

The demand for oxygen is very high in the retina. The needed oxygen production rate is defined in some applications by retinal oxygen demand. Human retinal oxygen consumption has been difficult to measure directly, and therefore a model is used for the whole retina when the inner part of the retina is subjected to different degrees of ischemia, retinal blood flow is automatically regulated in an attempt to maintain normal oxygen delivery. When the availability of oxygen is limited, the oxygen consumption is set to obey Michaelis-Menton kinetics.

Therefore the following parameters and formula may be used to determine the sufficient amount of oxygen to supply to the retina to meet retinal demand:

Parameter definitions:

Formula for human retinal consumption:

$$dp/dt = del(D_{ox}\ del\ p) - q_{ox} + s_{ox} \qquad \text{I}$$

$$q_{ox} = (p \cdot q_{oxmax})/(p + K_{ox})$$

$$s_{ox} = (bf/60) \cdot [(p^{blood} - \beta_{ox} \cdot p) + ((p^{blood})^n/((p^{blood})^n + (K_{hem})^n) - (\beta_{ox} \cdot p)^n/((\beta_{ox} \cdot p)^n) + (K_{hem})^n)) \cdot (Hb \cdot \delta)/\alpha_1]$$

In other aspects of the present invention injectable hyaluronic acid or nano-packaged hydrogen peroxide with a bio compatible catalase or enzyme/catalyst that releases $O_2$ on a renewable basis may be employed. This or some other chemical reaction such as $H_2O_2$ could be encapsulated in Hyaluronic Acid or a bio compatible nano encapsulation. Both are devices capable of generating $O_2$ from chemical reactions, to deliver oxygen into the eye, and an envelope much like that of FIG. 4 might be used, in some cases without electrodes and power supply, and in some cases with.

In particular, such a system and method may be used for the treatment of retinopathy, which occurs in patients with diabetes, sickle cell disease, retinopathy of prematurity, age-related macular degeneration, familial exudative retinopathy, retinal vascular occlusions, ocular ischemic syndrome, and other related conditions that have in common regional or diffuse retinal hypoxia. There are other conditions which can be treated with oxygen, including, for example, the cornea.

In systems which produce hydrogen as a by-product, such as electrolytic systems, the system may include venting mechanisms to eliminate hydrogen. In systems, which use air as a source for electrochemical extraction of oxygen, an inlet port may be included In another aspect injectable hyaluronic acid (HA) or other relatively inert agents may be used as a carrier or delivery vehicle of oxygenated material for oxygenating the interior of the human eye. Hyaluronic acid is presently used to maintain space in the open eye while surgery occurs, and is absorbed within three (3) months by the eye (which may be an optimal time period for healing of a retina, for example). For example, using a nano-bead with a slow diffusion gradient, oxygen may be diffused into the retina over a 90 day period.

It will be apparent to the skilled artisan that many alterations may be made to the embodiments described herein

| | |
|---|---|
| $\alpha_1$ | The solubility of oxygen in blood, equal to $1.5 \times 10^3$ |
| $\alpha_2$ | The solubility of oxygen in retina, equal to $1.4 \times 10^{-5}$ |
| $\beta_{ox}$ | The ratio of the partial pressures of oxygen in venous blood and retina (at steady state). (1) |
| Hf | Local blood flow in the inner retina (in ml/g · m) |
| $D_{ox}$ | The diffusion coefficient of oxygen ($2 \times 10^{-5}$ cm$^2$/s) |
| $\delta$ | The oxygen carrying capacity of hemoglobin (0.0616 mmol/g) |
| Hb | The hemoglobin concentration in blood (140 g/l) |
| $K_{hem}$ | A constant which equals the partial pressure of oxygen at which hemoglobin is 50% saturated with oxygen (26 mmHg) |
| $K_{ox}$ | The partial pressure of oxygen at which the consumption runs at half maximal speed (2 mmHg) |
| n | The Hill coefficient (2.7) |
| p | The local partial pressure of oxygen in retina (in mmHg) |
| $p^{blood}$ | The partial pressure of oxygen in arterial blood (80, 250, 405 mmHg) |
| $q_{ox}$ | The total local consumption of oxygen (in mmHg/s) |
| $q_{oxmax}$ | The maximal consumption rate of oxygen. [Inner retina: 26; Outer retina: 90 (light), 170 (dark) mmHg/s] |
| $S_{ox}$ | The amount of oxygen per unit time transferred locally from the blood to retina (in mmHg/s) | without departing from the spirit and scope of the invention. Sizes and materials may vary. Means of injection and implantation may vary. Different oxygen-producing materials may be used, all within the spirit and scope of the invention. The invention is to be defined, therefore, only by the scope of the claims which follow:

I claim:

1. An oxygen-producing device, comprising:
   a power supply with an electrically positive and an electrically negative output;
   at least one pair of electrodes, one electrode of the pair coupled to the electrically positive output and the other coupled to the electrically negative output;
   an oxygen-rich material exposed to the electrodes for producing oxygen in response to a voltage generated across the electrodes; and
   an envelope containing, the pair of electrodes and the oxygen rich material;
   characterized in that the device is configured to fit within a human eye without obstructing vision, the envelope comprises a gas-permeable membrane for releasing the produced oxygen into an environment outside of the envelope and the power supply is enabled to provide the voltage of at least 1.2 volts DC to the electrodes.

2. The device of claim 1 wherein the power supply comprises a battery rechargeable by magnetic induction.

3. The device of claim 1 wherein the power supply comprises a pair of cantilevered strips coupled to the electrodes, one of which strips is composed at least in part of a radioactive material that emits electrons, and the other is a metal strip, such that electrons emitted from the first strip collect on the second strip producing an electrical potential that appears across the electrodes.

4. The device of claim 3 wherein at least one of the strips is of a flexibility that the opposite charges cause the flexible strip to deflect toward the other strip, resulting over time in a proximity of the strips that results in discharge of the potential, after which the flexible strip returns to the un-deflected state, and the charge begins to rebuild.

5. The device of claim 1 wherein the oxygen-rich material is a liquid of water or hydrogen peroxide.

* * * * *